United States Patent [19]

Turcotte

[11] 4,418,214

[45] Nov. 29, 1983

[54] HYDROGEN RECOVERY BY ALCOHOL SCRUBBING IN ALCOHOL AMINATION

[75] Inventor: Michael G. Turcotte, Allentown, Pa.

[73] Assignee: Air Products and Chemicals, Inc., Allentown, Pa.

[21] Appl. No.: 434,768

[22] Filed: Oct. 18, 1982

[51] Int. Cl.$^3$ ............................................. C07C 85/06
[52] U.S. Cl. .................................... 564/479; 564/480
[58] Field of Search .............................. 564/479, 480

[56] References Cited

U.S. PATENT DOCUMENTS

| | | | |
|---|---|---|---|
| 2,053,193 | 9/1936 | Guinot | 564/480 X |
| 2,098,289 | 11/1937 | Greenewalt | 564/479 |
| 2,182,807 | 12/1939 | Hasche | 564/479 X |
| 2,312,754 | 3/1943 | Davy | 564/480 |
| 2,365,721 | 12/1944 | Olin et al. | 260/585 |
| 3,137,730 | 6/1964 | Fitz-William | 564/480 |
| 3,155,657 | 11/1964 | Bedoit | 564/480 X |
| 3,420,828 | 1/1969 | Muhlbauer | 260/247.7 |
| 3,720,715 | 3/1973 | Nicholl | 564/479 |
| 3,803,239 | 4/1974 | Feichtinger et al. | 564/480 X |
| 4,310,697 | 1/1982 | Cheminal et al. | 564/479 |

*Primary Examiner*—Paul F. Shaver

*Attorney, Agent, or Firm*—Michael Leach; E. Eugene Innis; James C. Simmons

[57] ABSTRACT

In a process for the preparation of alkylamines which comprises contacting an alkanol feed having at least three carbon atoms with ammonia in the presence of a hydrogenation catalyst and hydrogen in a reaction zone to yield a product effluent stream, separating the product effluent stream into an alkylamine stream for distillation and a vent stream comprising hydrogen and hydrocarbon by-products, the method comprising (a) contacting the hydrogen and hydrocarbon by-products vent stream in an absorber with an alkanol which is the same as the alkanol feed to yield a hydrogen gas stream and an alkanol wash stream containing the hydrocarbons, (b) recycling the hydrogen gas stream to the reaction zone, (c) stripping the alkanol wash stream in a stripper to provide a hydrocarbon waste stream and a regenerated alkanol stream, and (d) recycling the regenerated alkanol stream to the reaction zone.

6 Claims, 1 Drawing Figure

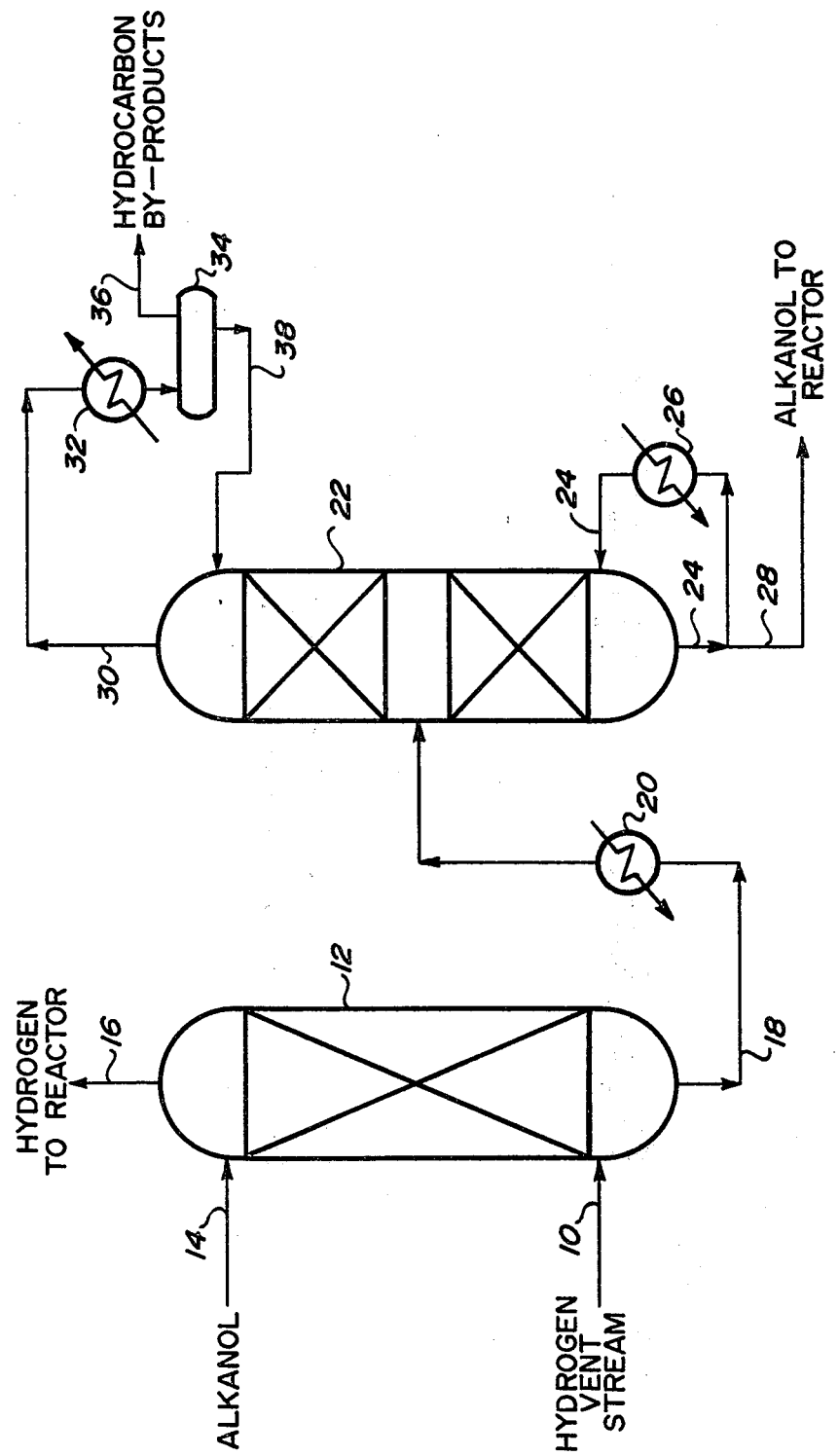

HYDROGEN RECOVERY BY ALCOHOL SCRUBBING IN ALCOHOL AMINATION

TECHNICAL FIELD

The invention relates to a process for the preparation of alkylamines by the amination of an alkanol. More particularly, the invention relates to a process for reacting an alkanol with ammonia in the presence of a hydrogenation catalyst and hydrogen.

BACKGROUND OF THE INVENTION

As is well known in the art, alkylamines can be prepared by reacting an alkanol with ammonia in the presence of hydrogen over a hydrogenation catalyst. The alkylamine products which are usually less volatile than ammonia or hydrogen can be condensed prior to effecting a separation between the unreacted ammonia and hydrogen. It is often the case that both the ammonia and the hydrogen streams are recycled to the amination reactor, but the formation of hydrocarbons as a by-product of the reaction contaminates the hydrogen stream and requires that the hydrogen and these by-products be vented to control hydrocarbon build-up. For example, in processes for the preparation of monoisopropylamine and diisobutylamine, hydrocarbons are produced to the extent that they must be removed from the hydrogen vent stream if hydrogen is to be recycled to the amination reaction. Increasing cost for hydrogen over the past several years makes it desirable to recover the hydrogen from the gaseous vent for recycling.

U.S. Pat. No. 2,365,721 discloses the preparation of amines by reacting $C_2$–$C_8$ alkanols with ammonia in the presence of hydrogen over a hydrogenation catalyst. The amine products which are less volatile than ammonia are condensed and separated from the ammonia and hydrogen which is then passed through an activated charcoal adsorber to remove any less volatile reaction products along with part of the ammonia. The remaining ammonia and hydrogen are then recirculated with a further quantity of the alkanol to the reaction.

U.S. Pat. No. 3,420,828 discloses a process for producing N-methoxyethylmorpholine in which the reaction product stream is separated in a separator to provide for the removal of hydrogen as an overhead for recycling to the reactor.

U.S. Pat. No. 3,710,715 discloses a process for the production of methylamines by the ammonolysis of methanol in the vapor phase. The process stream from the reactor is cooled and residual hydrogen and a small amount of ammonia are flashed off in a flash drum for recycling.

U.S. Pat. No. 4,310,697 describes a process for the preparation of dimethylethylamine by the reaction of ethanol with dimethylamine in the presence of hydrogen and a hydrogenation/dehydrogenation catalyst. The gaseous reaction effluent is cooled in a series of water-cooled condensers and then separated in a separator to provide a liquid product stream and an uncondensed gas stream of essentially hydrogen and 1 to 2% dimethylethylamine. The gas stream is recycled to the reactor after passing through an absorption column which can function either as a washer (by spraying the gas loaded with amine with water or ethanol), or to rid the gas of all liquid particles.

SUMMARY OF THE INVENTION

According to the invention a method is provided for the purification, recovery and recycling of hydrogen from a vent stream in a process for the preparation of higher alkylamines. The invention relates to a process for the preparation of alkylamines which comprises contacting a $C_3$–$C_6$ alkanol feed with ammonia in the presence of a hydrogenation catalyst and hydrogen in a reaction zone to yield a product effluent stream, and separating the product effluent stream into an alkylamine product stream for distillation and a vent stream comprising hydrogen and hydrocarbon by-products. The invention resides in the method which comprises
  (a) contacting the hydrogen and hydrocarbon by-product vent stream with an alkanol which is the same as that composing the alkanol feed to yield a hydrogen gas stream and an alkanol wash containing hydrocarbons,
  (b) recycling the hydrogen gas stream to the reaction zone,
  (c) stripping the alkanol wash to provide a hydrocarbon waste stream and a regenerated alkanol stream, and
  (d) recycling the regenerated alkanol stream to the reaction zone.

As an advantage of the invention, the use of the process alkanol feed as a scrubbing agent avoids introducing a foreign material into the amination process.

Hydrocarbons are removed from the gaseous hydrogen-containing vent stream by contacting the vent stream with the alkanol scrubbing agent in a conventional absorber. Any hydrocarbon heavier than ethane, for example propane, butane, isobutane and the like, is substantially absorbed into the liquid alkanol wash stream. The purified hydrogen which contains traces of the lighter hydrocarbons, such as methane and ethane, and alkanol is recycled to the process via a compressor. A small purge can be used to control any buildup of the lighter hydrocarbons.

A distillation column separates the hydrocarbons and the alkanol. The overhead rich in hydrocarbons is disposed of and the bottoms of almost pure alkanol is returned to the process as the alkanol feed. As a further advantage of the invention, the energy used in this column serves to preheat the alkanol feed.

BRIEF DESCRIPTION OF THE DRAWING

The sole FIGURE is a flow diagram of apparatus for practicing the method of the invention.

DETAILED DESCRIPTION OF THE INVENTION

In processes for the preparation of higher alkylamines, alkanols having at least 3 carbon atoms are vaporized and contacted with ammonia at a temperature ranging from 175° to 260° C. and a pressure ranging from 15 to 25 atm in the presence of a hydrogenation catalyst and hydrogen as is well known in the art. Generally, the alkanol:ammonia:hydrogen molar feed ratios may vary between 2:1:0.5 and 1:10:3 depending upon the desired alkylamine or catalyst. A high ratio of alkanol to ammonia will favor the trisubstituted alkylamine. Hydrogen is used to maintain catalytic activity, the amount depending on the process, reactor conditions and catalyst.

Representative of suitable hydrogenation catalysts for the alcohol amination process are the Group VIII B metals, particularly cobalt and nickel.

In order to produce the higher alkylamines the alkanol feed is a higher alkanol of at least 3 carbons, preferably a $C_3$–$C_6$ alkanol. As examples of suitable alkanols there are mentioned n-propanol, iso-propanol, n-butanol, iso-butanol, sec-butanol, n-pentanol, n-hexanol, and the like.

The product effluent stream from the amination reaction zone normally comprises the mono-, di-, and trialkylamines in a ratio which is dependent upon the alkanol:ammonia molar feed ratio and the recycle ratio of the undesired alkylamines. In other words, the desired alkylamine is separated from the reaction effluent stream and the undesired alkylamines are recycled to the reaction zone to generate the desired alkylamine product via the thermal equilibrium reactions.

In addition to the alkylamine product, the reaction effluent stream typically contains water vapor, unreacted alkanol, unreacted ammonia, hydrogen and hydrocarbon by-products. A preliminary separation may be performed in a vent separator which is a vapor-liquid separator. The gaseous stream from the vent separator is usually recycled to the reactor to reduce the hydrogen feed, but a purge is needed to remove the hydrocarbons and control their build-up in the system. Ammonia is recovered from this purge in a water absorber which results in a vent stream that is mostly hydrogen and hydrocarbon by-products since neither is soluble in the water. The vent stream may comprise from 60 to 90% hydrogen and 40 to 10% hydrocarbons. The liquid streams from the vent separator and the water absorber comprise the alkylamines, ammonia and water and are passed into a distillation train where water is separated for discard and the desired alkylamine products are obtained in substantially pure form. The unreacted ammonia together with the undesired alkylamines, if any, are recycled from the distillation train to the reaction zone.

While previously the vent stream substantially comprising hydrogen and hydrocarbon by-products was vented to the atmosphere or preferably thermally oxidized prior to venting to the atmosphere, the present invention provides a method for purifying the hydrogen and recycling it to the reaction zone. The vent stream is intimately mixed with an alkanol scrub stream, for example countercurrently in a conventional gas-liquid absorption column operating at a temperature from 15° to 35° C., or essentially ambient temperature, and a pressure from 15 to 25 atmospheres, or preferably as close to the reactor pressure as is practicable. For a vent stream flowing at a rate of about 450 liters/minute, a suitable flow rate for the alkanol scrub stream would be 50 to 100 liters/minute. The hydrocarbons in the gaseous vent stream are substantially absorbed into the liquid alkanol yielding a loaded alkanol scrub bottoms with an essentially clean hydrogen overhead. The loaded alkanol is stripped of the hydrocarbons in a conventional stripping column at 30° to 225° C. and 15 to 25 atmospheres using, for example, an indirectly steam heated reboiler. The stripped hydrocarbons are preferably discarded to the atmosphere by burning. The regenerated alkanol and the clean hydrogen are recycled to the amination reaction zone.

Prior to treating the hydrogen and hydrocarbon vent stream in the alkanol absorber, the vent stream ideally is washed in a water wash column to remove most of the ammonia from the vent stream. The ammoniacal water wash is combined with the liquid stream from the vent separator for processing in the distillation train.

Desirably, the alkanol scrub stream is an anhydrous liquid although aqueous alkanol solutions containing up to 7 wt.% water can be used, especially downstream of an ammonia water wash. Aqueous alkanol is not as desirable because the presence of water reduces the solubility of hydrocarbons in the scrubbing liquid.

Referring now to the FIGURE, the hydrogen and hydrocarbon-containing vent stream from an alkylamines process, not shown, is passed by line 10 into an absorber 12 where it is countercurrently contacted by an alkanol wash stream fed by line 14. The alkanol wash corresponds to the alkanol which is the feed to the amination reaction zone. In the absorber the alkanol wash removes, or scrubs, substantially all the hydrocarbons from the vent stream yielding an overhead stream 16 substantially comprising purified hydrogen. The recovered-purified hydrogen stream is then recompressed and recycled to the reaction zone, not shown.

The alkanol wash stream exiting absorber 12 in line 18 contains most of the hydrocarbon by-products originally present in the vent stream. The wash stream is heated by passage through heat exchanger 20 prior to entering stripper 22 where the hydrocarbons are thermally driven out of the alkanol. This stripping is accomplished by having alkanol stream 24 from the bottoms of stripper 22 pass through heat exchanger 26 which acts like a reboiler to provide the thermal energy for expelling the absorbed hydrocarbons from the alkanol. A portion of the alkanol stream from the bottoms of stripper 22 is removed in line 26 for cycling to the amination reaction zone.

An overhead gas stream comprising essentially hydrocarbons and a minor amount of alkanol in line 30 is conveyed to a condenser 32 where the overhead stream is cooled and passed into separator 34. The purge gas stream in line 36 comprising the hydrocarbons exits separator 34 for venting to the atmosphere or preferably for thermal oxidation. Condensed hydrocarbons and alkanol from separator 34 are pumped by line 38 back into stripper 22 as a reflux.

Table 1 gives the process parameters for the treatment of a hydrogen and hydrocarbon containing vent stream emanating from a process for the amination of isopropanol using a cobalt catalyst to yield monoisopropylamine (MIPA) as the desired product. The principal hydrocarbon by-products are methane and propane in this MIPA process. Isopropanol is introduced as the alcohol scrub material in line 14. In calculating the data shown in Table 1, solubilities of hydrogen and the hydrocarbons in the alkanol were determined by K-factors from A. I. El-Twaty and J. M. Prausnitz, "Correlation of K-Factors for Mixtures of Hydrogen and Heavy Hydrocarbons", Chemical Engineering Science, Vol. 35, pp 1765–1768, Pergamon Press Ltd., 1980. The data in the table shows that recovered hydrogen stream 16 is substantially pure hydrogen containing minor amounts of methane, propane and isopropanol. The recovered alkanol in line 28 is essentially pure isopropanol which will be conveyed to the amination reaction zone.

TABLE 1

| Stream Number | 10 | 14 | 16 | 18 | 28 | 36 | 38 |
|---|---|---|---|---|---|---|---|
| Stream Name | Amination Vent | Alcohol Scrub | Recovered Hydrogen | Scrubber Bottoms | Recovered Alcohol | Purge Gas | Stripper Reflux |
| Component (mole/hr) | | | | | | | |
| Hydrogen | 30.4 | — | 28.4 | 2.0 | — | 2.0 | 0.1 |
| Methane | 4.4 | — | 0.6 | 3.8 | — | 3.8 | 1.4 |
| Propane | 3.9 | — | 0.1 | 3.8 | — | 3.8 | 6.2 |
| Butane | — | — | — | — | — | — | — |
| Isopropanol | — | 125 | 0.1 | 124.9 | 124.8 | 0.1 | 7.3 |
| Total | 38.7 | 125 | 29.2 | 134.5 | 124.8 | 9.7 | 15.0 |
| Temperature (°F.) | 90 | 80 | 80 | 86 | 355 | 100 | 100 |
| Pressure (psia) | 240 | 240 | 240 | 240 | 240 | 240 | |

TABLE 2

| Stream Number | 10 | 14 | 16 | 18 | 28 | 36 | 38 |
|---|---|---|---|---|---|---|---|
| Stream Name | Amination Vent | Alcohol Scrub | Recovered Hydrogen | Scrubber Bottoms | Recovered Alcohol | Purge Gas | Stripper Reflux |
| Component (mole/hr) | | | | | | | |
| Hydrogen | 30.1 | — | 28.6 | 1.5 | — | 1.5 | 0.1 |
| Methane | 2.2 | — | 0.3 | 1.9 | — | 1.9 | 0.7 |
| Propane | 1.9 | — | — | 1.9 | — | 1.9 | 3.0 |
| i-Butane | 3.8 | — | — | 3.8 | — | 3.8 | 9.0 |
| Isobutanol | — | 40 | 0.1 | 39.9 | 39.8 | 0.1 | 2.2 |
| Total | 38.0 | 40 | 29.0 | 49.0 | 39.8 | 9.2 | 15.0 |
| Temperature (°F.) | 90 | 80 | 80 | 90 | 395 | 100 | 100 |
| Pressure (psia) | 240 | 240 | 240 | 240 | 240 | 240 | 240 |

Table 2 shows the process parameters for a hydrogen and hydrocarbon containing vent stream from a process for reacting isobutanol and ammonia in the presence of hydrogen and a nickel catalyst to yield diisobutylamine (DIBA). Again the solubilities of hydrogen and the hydrocarbons in the isobutanol scrub which were used in determining the data shown in Table 2, were determined by K-factor from the El-Twaty and Prausnitz publication. The data in Table 2 shows that the treatment of a hydrogen vent stream from the DIBA process according to the method of the present invention yields a recovered hydrogen stream for recycling which is substantially pure hydrogen with very small amounts of methane and isobutanol.

The described process is limited to alkanol amination in which the alkanol comprises at least 3 carbon atoms. This limitation is necessary because the lower alkanols, methanol and ethanol, do not absorb the hydrocarbon by-products to the extent required at reasonable operating conditions to afford a sufficiently cleaned hydrogen recycle stream. Amination of alkanols having moe than 6 carbon atoms would not especially benefit from the scrubbing process because the hydrocarbon by-products formed in such processes would pass into the vent separator liquid.

From the above examples it can be seen that the invention provides a method for enriching and recycling hydrogen which is currently vented in higher amines processes and thus reduces hydrogen consumption. This recycling is made possible by the separation of hydrogen from the by-product hydrocarbon gases. The process offers advantage from an environmental standpoint as it reduces the quantities of vent gases that must be incinerated and can be used to provide a moderate increase in the hydrogen:alkanol ratio, reducing by-product formation.

STATEMENT OF INDUSTRIAL APPLICATION

A method is provided for recovery, purification and recycle of hydrogen from the hydrogen and hydrocarbon-containing vent gas stream in a higher alkylamines process. Higher alkylamines such as monoisopropylamine and diisobutylamine are useful chemical intermediates in the manufacture of herbicides.

I claim:

1. In a process for the preparation of alkylamines which comprises contacting an alkanol feed having at least three carbon atoms with ammonia in the presence of a hydrogenation catalyst and hydrogen in a reaction zone to yield a product effluent stream, and separating the product effluent stream into an alkylamine stream for distillation and a vent stream comprising hydrogen and hydrocarbon by-products, the method comprising
   (a) contacting the hydrogen and hydrocarbon by-products vent stream with an alkanol which is the same as the alkanol feed to the reaction zone, to yield a hydrogen gas stream and an alkanol wash stream containing the hydrocarbons,
   (b) recycling the hydrogen gas stream to the reaction zone,
   (c) stripping the alkanol wash stream to provide a hydrocarbon waste stream and a regenerated alkanol stream, and
   (d) recycling the regenerated alkanol stream to the reaction zone.

2. The invention of claim 1 in which the alkanol is a $C_3$–$C_6$ alkanol.

3. The invention of claim 1 in which the alkanol is isopropanol.

4. The invention of claim 1 in which the alkanol is isobutanol.

5. The invention of claim 1 in which the vent stream is washed with water to remove ammonia prior to step (a).

6. In a process for the preparation of alkylamines which comprises contacting an alkanol feed which is isopropanol or isobutanol with ammonia in the presence of a hydrogenation catalyst and hydrogen in a reaction zone to yield a reaction effluent stream, and separating the reaction effluent stream into an alkylamine stream for distillation and a vent stream comprising hydrogen and hydrocarbon by-products, the method comprising:

(a) contacting the hydrogen and hydrocarbon by-products vent stream with an alkanol which is the same as the alkanol feed to the reaction zone at a temperature from 15° to 35° C. and a pressure from 15 to 25 atmospheres, to yield a hydrogen gas stream and an alkanol wash stream containing the hydrocarbons, (b) recycling the hydrogen gas stream to the reaction zone, (c) stripping the alkanol wash stream at a temperature from 30° to 225° C. to provide a hydrocarbon waste stream and a regenerated alkanol stream, and (d) recycling the regenerated alkanol stream to the reaction zone.

* * * * *